United States Patent [19]

Whitehouse et al.

[11] Patent Number: 5,690,487
[45] Date of Patent: Nov. 25, 1997

[54] DISPOSABLE ORAL SUCTION TIP

[75] Inventors: Ronald L. S. Whitehouse; Connie Watson, both of Edmonton, Canada

[73] Assignee: White Shield Inc., Edmonton, Canada

[21] Appl. No.: 745,675

[22] Filed: Nov. 8, 1996

Related U.S. Application Data

[63] Continuation of Ser. No. 418,404, Apr. 7, 1995, abandoned.

[51] Int. Cl.⁶ .................................................. A61C 17/06
[52] U.S. Cl. ................................................ 433/91; 433/96
[58] Field of Search ............................. 433/91, 93, 94, 433/95, 96; 604/119, 902

[56] References Cited

U.S. PATENT DOCUMENTS

| | | | |
|---|---|---|---|
| 417,874 | 11/1889 | Anderson et al. | 433/96 |
| 1,222,267 | 4/1917 | Cosad | 433/91 |
| 1,388,312 | 8/1921 | Seeger | 433/96 |
| 1,930,196 | 10/1933 | Fisher | 433/94 |
| 2,529,499 | 11/1950 | Jankelson | 433/96 |
| 2,574,135 | 11/1951 | Ward | 433/96 |
| 3,256,885 | 6/1966 | Higgins et al. | 433/91 |
| 3,453,735 | 7/1969 | Burt | 433/96 |
| 3,455,324 | 7/1969 | Bieri et al. | |
| 3,516,160 | 6/1970 | Leffler | 433/95 |
| 3,541,583 | 11/1970 | Deuschle | 433/96 |
| 3,881,254 | 5/1975 | Epstein | 433/96 |
| 4,221,220 | 9/1980 | Hansen | 433/95 |
| 4,487,600 | 12/1984 | Brownlie | 604/119 |
| 5,080,587 | 1/1992 | Miyao | 433/91 |
| 5,094,616 | 3/1992 | Levenson | 433/91 |
| 5,123,840 | 6/1992 | Nates | 433/91 |
| 5,195,952 | 3/1993 | Solnit et al. | 433/91 |

FOREIGN PATENT DOCUMENTS

| | | | |
|---|---|---|---|
| 456483 | 11/1936 | United Kingdom | 433/91 |
| 2058576 | 4/1981 | United Kingdom | 433/95 |

OTHER PUBLICATIONS

Article published in The Journal of The American Dental Association vol. 124 Apr. 1993 entitled Possibility of Cross--Contamination Between Dental Patients By Means of the Saliva Ejector by C. M. Watson, R.D.H.; R.L.S. Whitehouse, PH.D.

*Primary Examiner*—Cary E. O'Connor
*Attorney, Agent, or Firm*—Davis and Bujold

[57] ABSTRACT

A disposable oral suction tip includes a tubular body having a suction line attachment end, a mouthpiece end, an exterior surface and at least one central passage that extends between the suction line attachment end and the mouthpiece end. A mouthpiece is secured to the mouthpiece end of the tubular body. At least one vacuum release channel is provided having a first end and a second end. The at least one vacuum release channel extends along the exterior surface of the tubular body. The first end of the at least one vacuum release channel is positioned to be placed into a patient's mouth along with the mouthpiece. The second end is spaced from the mouthpiece such that the at least one vacuum release channel provides direct venting of the oral cavity.

4 Claims, 1 Drawing Sheet

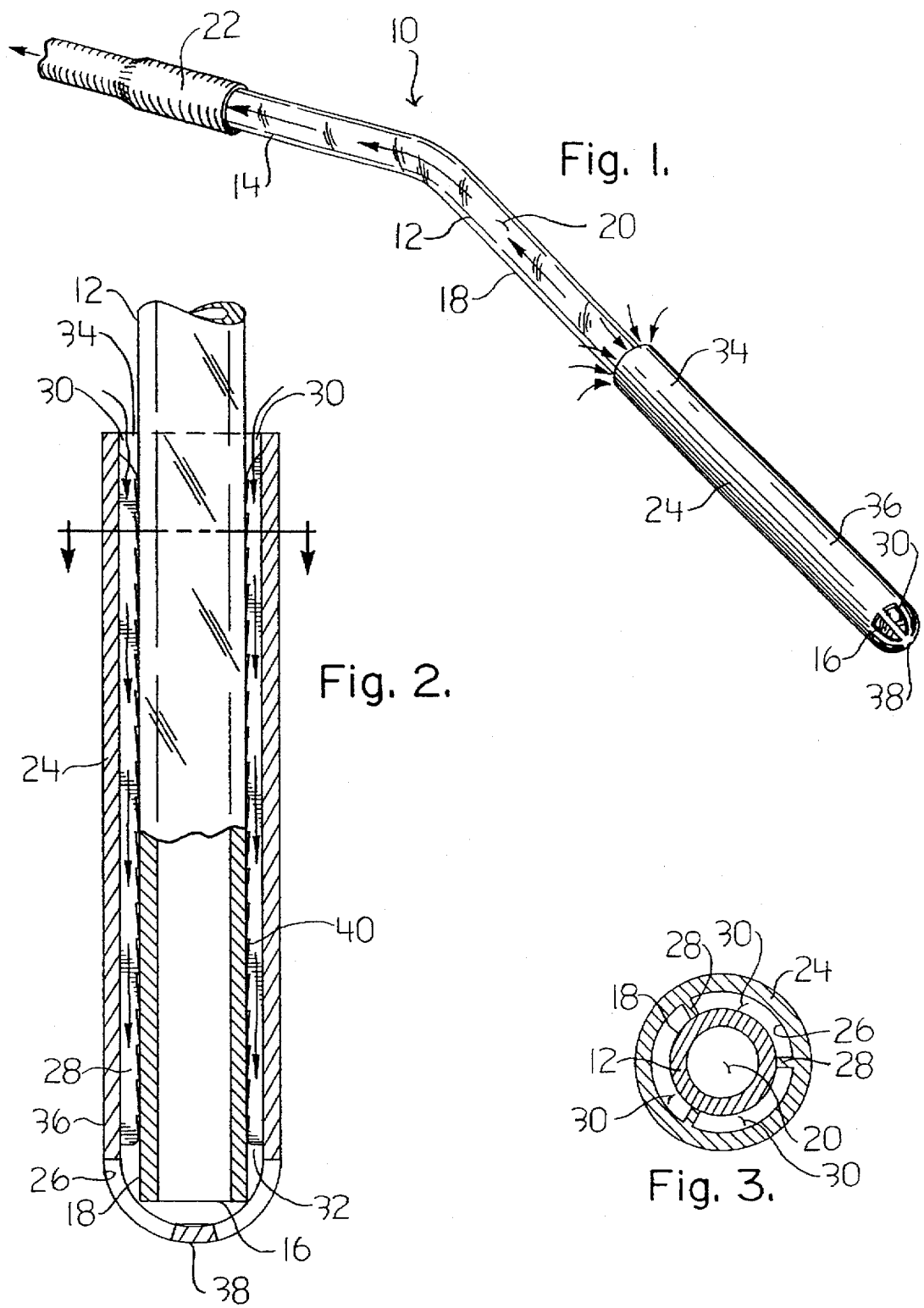

DISPOSABLE ORAL SUCTION TIP

This application is a continuation of application Ser. No. 08/418,404 filed on Apr. 7, 1995, now abandoned.

FIELD OF THE INVENTION

The present invention relates to a disposable oral suction tip used on a dental office suction line to prevent cross-contamination between patients.

BACKGROUND OF THE INVENTION

In the April 1993 edition of the Journal of the American Dental Association, Watson and Whitehouse published the results of a study regarding hygienic procedures in dental offices in a paper entitled "Possibility of Cross-contamination between Dental Patients by means of the Saliva Ejector". Prior to the study by Watson and Whitehouse it had been felt that disposal and replacement of the oral suction tip was sufficient protection for the patient. Watson and Whitehouse documented that, when a patient closes his or her lips around the oral suction tip, a higher vacuum can be temporarily created in the mouth than in the suction line. This can result in a back flow of fluid from the suction line, through the oral suction tip, and into the mouth of the patient. When such a back flow occurs there is a danger that oral contaminants from a previous patient will be drawn into the mouth of the current patient. This raised the possibility of a cross-contamination occurring between patients, and demonstrated the need to re-evaluate sanitation and hygienic practises in dental offices.

U.S. Pat. No. 5,425,637, which issued to Watson and Whitehouse, discloses a disposable oral suction tip which has been modified to reduce or eliminate the possibility of cross-contamination occurring between patients. The modification includes at least one unregulated vacuum release aperture through the tubular sidewall of the oral suction tip. This aperture is spaced from the mouthpiece such that when the mouthpiece is inserted into a patient's mouth, the patient's mouth will not block the aperture. The solution proposed by Watson and Whitehouse is effective if the oral suction tip is used as directed. However, the presence of the vacuum release aperture reduces the amount of suction force available; which can be a drawback with low volume suction lines.

SUMMARY OF THE INVENTION

What is required is an oral suction tip that addresses the problem of patient cross-contamination without adversely affecting the suction force available.

According to the present invention there is provided a disposable oral suction tip which includes a tubular body having a suction line attachment end, a mouthpiece end, an exterior surface and at least one central passage that extends between the suction line attachment end and the mouthpiece end. A mouthpiece is secured to the mouthpiece end of the tubular body. At least one vacuum release channel is provided having a first end and a second end. The at least one vacuum release channel extends along the exterior surface of the tubular body. The first end of the at least one vacuum release channel communicates with the mouthpiece. The second end is spaced from the mouthpiece such that the at least one vacuum release channel provides direct venting of the oral cavity.

The disposable oral suction tip, as described above, provides direct venting of the oral cavity to prevent a vacuum buildup that is capable of drawing contaminants from the suction line into the oral cavity. As the vacuum release channel runs along the exterior surface of the tubular body and is not connected to the suction source, there is no effect upon the force of suction up the at least one central passage.

The preferred configuration involves positioning a tubular barrel having an internal surface with a plurality of internal vanes over the tubular body. The internal vanes divide a space between the internal surface of the tubular barrel and the exterior surface of the tubular body into a plurality of the vacuum release channels. The tubular barrel can be provided with an end that is integrally formed to serve as the mouthpiece.

Although beneficial results may be obtained through the use of the disposable oral suction tip, as described above, the separation of the tubular barrel from the tubular body would pose a danger to the patient. Even more beneficial results may, therefore, be provided when the internal vanes have peripheral edges that form a gripping surface to resist removal of the tubular barrel from over the tubular body.

BRIEF DESCRIPTION OF THE DRAWINGS

These and other features of the invention will become more apparent from the following description in which reference is made to the appended drawings, wherein:

FIG. 1 is a perspective view of a disposable oral suction tip constructed in accordance with the teachings of the present invention.

FIG. 2 is a side elevation view in longitudinal section of the disposable oral suction tip illustrated in FIG. 1.

FIG. 3 is an end elevation view in transverse section of the disposable oral suction tip illustrated in FIG. 1.

DETAILED DESCRIPTION OF THE PREFERRED EMBODIMENT

The preferred embodiment, a disposable oral suction tip generally identified by reference numeral 10, will now be described with reference to FIGS. 1 through 3.

Referring to FIG. 1, disposable oral suction tip 10 has a bendable plastic tubular body 12 having a suction line attachment end 14 and a mouthpiece end 16. Tubular body 12 has an exterior surface 18 and a central passage 20 that extends between suction line attachment end 14 and mouthpiece end 16. Suction line attachment end 14 is attached to a suction line 22 during use. Referring to FIGS. 2 and 3, a tubular barrel 24 having an internal surface 26 with a plurality of internal vanes 28 overlies tubular body 12. Internal vanes 28 engage exterior surface 18 of tubular body 12 and divide a space between internal surface 26 of tubular barrel 24 and exterior surface 18 of tubular body 12 into a plurality of vacuum release channels 30 extending along exterior surface 18 of tubular body 12. Referring to FIG. 2, each of the vacuum release channels 30 has a first end 32 and a second end 34. First end 32 communicates with mouthpiece end 16 of tubular body 12. Second end 34 is spaced from mouthpiece end 16 of tubular body 12. Tubular barrel 24 has a mouthpiece end 36 that is integrally formed into a mouthpiece 38. Referring to FIG. 2, internal vanes 28 having peripheral edges that form a saw tooth gripping surface, generally designated by reference numeral 40.

The use and operation of disposable oral suction tip 10 will now be described with reference to FIGS. 1 through 3. Referring to FIG. 2, saw tooth gripping surface 40 plays an important role during assembly. It allows tubular barrel 24 to be slid over tubular body 12 in a first direction during assembly. However, saw tooth gripping surface 40 digs into exterior surface 18 of tubular body 12 to resist removal of tubular barrel body 24 from over tubular body 12 in a second direction. This is important as the dentist must have confidence that tubular barrel 24 will not separate from tubular body 12 during use and become lodged in the patient's throat. Referring to FIG. 1, suction line attachment end 14 of disposable oral suction tip 10 is attached to a suction line 22 in preparation for use. Mouthpiece 38 is then inserted into a patient's mouth. When in the patient's mouth, vacuum release channels 30 provide direct venting of the oral cavity, as indicated by arrows.

It will be apparent to one skilled in that art that disposable oral suction tip 10 addresses the problem of patient cross-contamination without adversely affecting the suction force available. In addition, with the preferred embodiment, a blockage of the vacuum release channels by either the patient's mouth or the dentist's hands is extremely unlikely, if not impossible. Accidental or intentional blockage of the vacuum release aperture in the prior art embodiments, would eliminate the protection against cross-contamination. Finally, it will be apparent to one skilled in the art that modifications may be made to the illustrated embodiment without departing from the spirit and scope of the invention as hereinafter defined in the claims.

The embodimnents of the invention in which an exclusive property or privilege is claimed are as follows:

1. A disposable oral suction tip, comprising:

a bendable tubular body having a consistent cross-sectional profile having a suction line attachment and attachable to a suction source, a mouthpiece end, an exterior surface and at least one central passage that extends between the suction line attachment end and the mouthpiece end;

a mouthpiece secured to the mouthpiece end of the tubular body where the mouthpiece is directly open to a plurality of vacuum release channels and the mouthpiece is directly open to the at least one central passage so that the plurality of vacuum release channels and the at least one central passage can communicate; and a tubular barrel having an internal surface with a plurality of internal vanes overlies the tubular body, the internal vanes dividing a space between the internal surface of the tubular barrel and the exterior surface of the tubular body into the plurality of vacuum release channels each of the plurality of vacuum release channels having a first end and a second end, each of the plurality of vacuum release channels extending along the exterior surface of the tubular body, the first end being positioned for placement in a patient's mouth along with the mouthpiece and the second end being spaced from the mouthpiece such that there is communication between the suction source and each of the plurality of vacuum release channels, so that when the patient's mouth is closed over the mouthpiece the plurality of vacuum release channels provide direct unobstructed venting of the oral cavity to prevent backflow from the at least one central passage into the patient's mouth and there is no effect on the force of suction up the at least one central passage.

2. A disposable oral suction tip, comprising:

a bendable tubular body having a suction line attachment end, a mouthpiece end, an exterior surface and at least one central passage that extends between the suction line attachment end and the mouthpiece end;

a mouthpiece secured to the mouthpiece end of the tubular body; and a tubular barrel having an internal surface with a plurality of internal vanes overlies the tubular body, the internal vanes dividing a space between the internal space of the tubular barrel and the exterior surface of the tubular body into a plurality of the vacuum release channels each of the plurality of vacuum release channels having a first end and a second end, each of the plurality of vacuum release channels extending alone the exterior surface of the tubular body, the first end being positioned for placement in a patient's mouth along with the mouthpiece and the second end being spaced from the mouthpiece such that each of the plurality of vacuum release channels provides direct venting of the oral cavity surface to resist removal of the tubular barrel from over the tubular body.

3. The disposable oral suction tip as defined in claim 2, wherein the tubular barrel has an end that is integrally formed into the mouthpiece.

4. A disposable oral suction tip, comprising:

a bendable tubular body having a suction line attachment end, a mouthpiece end, an exterior surface and at least one central passage that extends between the suction line attachment end and the mouthpiece end; and a tubular barrel having an internal surface with a plurality of internal vanes overlying the tubular body, the internal vanes dividing a space between the internal surface of the tubular barrel the exterior surface of the tubular body into a plurality of vacuum release channels extending along the exterior surface of the tubular body, each of the vacuum release channels having a first end and a second end, the first end communicating with the mouthpiece end of the tubular body and the second end being spaced from the mouthpiece end of the tubular body such that the vacuum release channels provide direct venting of the oral cavity, the tubular barrel having a mouthpiece end that is integrally formed into a mouthpiece, the internal vanes having peripheral edges that form a saw tooth gripping surface, the saw tooth gripping surface allowing the tubular barrel to be slid over the tubular body in a first direction, and digging into the exterior surface of the tubular body to resist removal of the tubular barrel from over the tubular body in a second direction.

* * * * *